(12) United States Patent  
Ainsworth et al.

(10) Patent No.: US 6,626,935 B1
(45) Date of Patent: Sep. 30, 2003

(54) INTRAVASCULAR STENT (75) Inventors: Stephen D. Ainsworth, Santa Clara, CA (US); E Tina Cheng, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 120 days.

(21) Appl. No.: 09/747,176

(22) Filed: Dec. 21, 2000

(51) Int. Cl.[7] ................................................. A61F 2/06
(52) U.S. Cl. ...................................... 623/1.15; 623/1.16
(58) Field of Search .............................. 623/1.15, 1.16, 623/1.17–1.22

(56) References Cited

U.S. PATENT DOCUMENTS

| | | | |
|---|---|---|---|
| 5,695,516 A | 12/1997 | Fischell et al. | |
| 5,697,971 A | 12/1997 | Fischell et al. | |
| 5,755,776 A | 5/1998 | Al-Saadon | |
| 5,843,175 A | 12/1998 | Frantzen | |
| 5,868,782 A * | 2/1999 | Frantzen | 128/899 |
| 5,911,754 A * | 6/1999 | Kanesaka et al. | 606/198 |
| 5,931,867 A | 8/1999 | Haindl | |
| 5,935,162 A | 8/1999 | Dang | |
| 6,019,789 A | 2/2000 | Dinh et al. | |
| 6,066,169 A | 5/2000 | McGuinness | |
| 6,083,259 A * | 7/2000 | Frantzen | 623/1.15 |
| 6,132,460 A | 10/2000 | Thompson | |
| 6,132,461 A | 10/2000 | Thompson | |
| 6,162,243 A | 12/2000 | Gray et al. | |
| 6,171,334 B1 | 1/2001 | Cox | |
| 6,190,405 B1 | 2/2001 | Culombo et al. | |
| 6,217,608 B1 * | 4/2001 | Penn et al. | 623/1.15 |

* cited by examiner

Primary Examiner—Corrine McDermott
Assistant Examiner—Hieu Phan
(74) Attorney, Agent, or Firm—Fulwider Patton Lee & Utecht, LLP

(57) ABSTRACT

This invention is directed to an expandable stent for implanting in a body lumen. The invention provides for an intravascular stent having cylindrical rings and a plurality of flexible spring joints linking the rings together. The flexible spring joints enable components of the stent to be large enough to provide excellent radiopaque and vessel supporting capabilities. The stent is flexible along its length and about its longitudinal axis while maintaining stiffness in the radial direction in order to resist collapse once implanted.

12 Claims, 5 Drawing Sheets

INTRAVASCULAR STENT

BACKGROUND OF THE INVENTION

This invention relates to devices for the treatment of heart disease and particularly to endo-arterial prostheses, which are commonly called stents. More particularly, the invention relates to stents incorporating flexible joints in the structure thereof that enable the stents to bend inside a patient's vasculature.

Several interventional treatment modalities are presently used for heart disease, including balloon and laser angioplasty, atherectomy, and by-pass surgery. In typical coronary balloon angioplasty procedures, a guiding catheter having a distal tip is percutaneously introduced through the femoral artery and advanced into the cardiovascular system of a patient using a conventional Seldinger technique and advanced within the cardiovascular system until the distal tip of the guiding catheter is seated in the ostium of a coronary artery. A guide wire is positioned within an inner lumen of a dilatation catheter and then both are advanced through the guiding catheter to the distal end thereof. The guide wire is first advanced out of the distal end of the guiding catheter into the patient's coronary vasculature until the distal end of the guide wire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion. Once in position across the lesion, the balloon is inflated to compress the plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guide wires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,451,233 (Yock); and U.S. Pat. No. 5,458,651 (Klemm, et al.), which are hereby incorporated herein in their entirety by reference thereto.

One problem that can occur during balloon angioplasty procedures is the formation of intimal flaps which can collapse and occlude the artery when the balloon is deflated at the end of the angioplasty procedure. Another problem characteristic of balloon angioplasty procedures is the large number of patients who are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent development work in the treatment of heart disease has been directed to endoprosthetic devices called stents. Stents are generally cylindrically shaped intravascular devices which are placed within an artery to hold it open. The device can be used to reduce the likelihood of restenosis and to maintain the patency of a blood vessel immediately after intravascular treatments. In some circumstances, they can also be used as the primary treatment device where they are expanded to dilate a stenosis and then left in place. Further details of stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); U.S. Pat. No. 4,886,062 (Wiktor); U.S. Pat. No. 5,421,955 (Lau); and U.S. Pat. No. 5,569,295 (Lam), which are hereby incorporated herein in their entirety by reference thereto.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

Advancing the stent through a patient's vasculature, which can involve traversing sharp bends and other obstacles, may require the stent to be highly flexible. Stent flexibility also permits the stent to be deployed in and conform to a tortuous section of a patient's vasculature. Additionally, visualizing the stent with a fluoroscope, which is currently the most widely used method of stent visualization during stent deployment, requires a stent with good radiopacity.

Different methods have been attempted to give stents high flexibility and radiopacity. By making stents out of relatively thin material, flexibility can be increased. However, the use of thin material can reduce the radiopacity of the stent, which can make it difficult for a physician or technician to visualize the stent. Conversely, the use of thicker material, which promotes radiopacity, can reduce stent flexibility and resultantly impair the deliverability of the stent.

An early attempt at achieving a flexible stent with good radiopacity characteristics involved providing a stent of a base material with good flexibility and strength but relatively low radiopacity, and then adding a thin layer of a highly-radiopaque material, such as gold, to the stent. This approach, which required the use of two separate materials, involved a relatively complicated process in applying the radiopaque material to the stent. Additionally, the use of multiple materials can complicate use and deployment of the stent, particularly where the different materials have different material characteristics, such as different strengths, different biocompatibility, or different responses to temperature changes.

Another approach was to provide a stent with substantially thicker portions at each end. Such an approach provided a stent with highly radiopaque ends, so that a physician could easily view the stent ends during stent delivery.

What has been needed and heretofore unavailable is an improved means of providing a stent with high flexibility, strength, and radiopacity. The present invention satisfies this need.

SUMMARY OF THE INVENTION

This invention relates to devices for the treatment of heart disease and particularly to endo-arterial prostheses, which are commonly called stents. More particularly, the invention relates to stents incorporating flexible joints in the structure thereof enabling the stents to easily bend to conform to a patient's vasculature.

Present day expandable stent designs incorporate portions that flex or otherwise deform during insertion of the stent into a patient's vasculature. Similarly, there are also portions of the stent that remain more stable (i.e., less deformed) during insertion.

It will be appreciated that as a stent advanced along a circuitous path in a coronary artery, it flexes about it longitudinal axis in order to navigate curves in the patient's vasculature. In this invention, when the stent is flexed while passing through the bends in an artery, some portions of the stent will flex substantially while other portions, remain less deformed. Thus, the stent has highly flexible portions and more stable (i.e., less deformed) portions that function accordingly during insertion into a patient's vasculature.

The flexibility of a stent upon insertion into a patient's vasculature is largely derived from highly flexible portions of the stent, without substantial assistance from the more rigid or stable portions. Stable portions in this case are those portions that, due to the overall stent design, will, when implanted at the implant site resiliently assume their distended circumferential configuration during insertion. Some of these portions are configured to flex under selected loads such as experienced during implantation. These stable portions provide strength to afford support to resist collapse from radially inwardly acting forces, but do not substantially flex or otherwise deform while the stent is inserted through the vasculature.

What makes the stent of the present invention highly flexible is the incorporation of flexible joints which couple the cylindrical rings to each other. The flexible joints, as described below are designed to be flexible and enable the stent, to, while being advanced to the implant site, flex significantly about the longitudinal axis. The resulting flexible stent can be more safely advanced through a patient's vasculature during delivery.

The stent of the present invention generally includes a plurality of radially expandable cylindrical rings which are relatively independent of one another in their ability to expand and flex relative to one another. Flexible joints enable the rings to behave accordingly. The flexible joints may be formed by the opposite extremities of connecting links joining adjacent cylindrical rings together. The links provide increased stability and help to prevent warping of the stent upon expansion and the springs enable the stent to flex to conform to a tortuous vessel. Either or both of the springs and links can be formed with smaller cross-sections or be formed of a selected material more flexible than the remainder of the cylindrical rings to enhance flexibility.

The resulting stent structure is a series of radially expandable cylindrical rings spaced longitudinally apart and connected to each other by the flexible joints formed by links and springs. Due to the flexibility of the springs which couple the links to the rings, the individual rings may rotate slightly relative to each other without significant deformation. Cumulatively, the stent is flexible along its length and about its longitudinal axis but is still relatively stiff in the radial direction in order to resist collapse once implanted.

One preferred structure for the expandable cylindrical rings is a generally circumferential undulating pattern, e.g., serpentine. The cylindrical rings typically are formed of a plurality of undulations defining peaks and valleys, where the valleys of one cylindrical ring can be circumferentially offset from the valleys of an adjacent cylindrical ring. In this configuration, at least one link attaches each cylindrical ring to an adjacent cylindrical ring so that one end of a link is positioned substantially within one of the valleys and the other end attaches the valley to a peak of an adjacent ring. When the rings are not circumferencially offset a valley can be connected through the flexible joint to a valley in an adjacent ring. In this configuration, both the peaks and valleys of adjacent rings will be longitudinally aligned with each other.

The rings themselves are formed by a series of U and/or W-shaped undulations disposed in a generally elongated cylindrical configuration and arranged in repeating patterns. While the cylindrical rings are not divided up or segmented into U's and/or W's, the pattern of the cylindrical rings resemble such a configuration. The longitudinal U and W patterns promote some flexibility in the stent by flexing and by tipping radially outwardly at one end or the other as the stent is flexed to curve in one direction or the other along its longitudinal axis as it is advanced along in a tortuous vessel. The flexibility during insertion though is generally limited due to the thickness required in the ring to afford resistance to radial collapse and present adequate radiopacity.

In order to balance the need for increased stent thickness driven by the radiopacity requirements mentioned above, with the need for flexibility/deployment requirements, the current invention provides a stent having flexible joints which include springs formed with undulations defined by smaller, sub peaks and valleys. These springs can couple the connecting links to the rings to allow for greater freedom of ring conformability. The links also can be connected at their respective one or both ends directly to the respective rings for structural rigidity purposes. Furthermore, each ring is generally formed with more than one spring so as to be interposed between segments of the respective rings. The springs are configured to provide for the adjacent cylindrical rings flexing and compressing with respect to each other to increase the stent's ability to flex and bend around tight or tortuous anatomy.

The rings are configured so the springs cooperate to enable the stent to flex longitudinally during and after stent expansion in order to conform to the vessel wall. This conformability has been shown though experimentation to reduce the likelihood of restenosis so when compared to stents which don't conform to the same degree. The springs cooperate to cause such rings to substantially retain their pre-insertion dimensions during and after insertion so as to retain their flexible characteristics.

The stent design of the current invention resists the tendency of twisting at one end of the stent to be transmitted along the length of the stent while it is being expanded in a vessel. Coupling the links to the rings at the respective springs serves to provide for lost rotary motion between adjacent ones of the rings. That is, as the stent is navigated through the circuitous vasculature, rotary forces may be applied to a ring at one end of the stent causing it to rotate slightly in one direction. The flexibility in the respective springs will result in such spring flexing slightly allowing the respective connecting link to angle in one direction or the other thus minimizing the tendency of such rotary force to be transmitted on to the adjacent ring. This lack of rotational translation from ring to ring serves to minimize the tendency of rotary forces applied to one end of the stent resulting in a bodily rotation of the entire stent and the resultant loss of control during placement at the implant site.

The sub peak and valley segments forming the springs can also comprise a series of U and/or W-shaped structures.

While not divided up or segmented into U and/or W segments, the pattern of the sub peaks and valleys resemble such a configuration. The flexibility is generally high because the transverse cross-sections of the springs are generally smaller than those of undulations in the rings. Such cross-sections may be small because there is generally less need for radiopaque properties, it being recognized that the cross-sections of the undulations can be larger so as to cooperate in meeting the radiopaque requirements discussed previously.

The stent embodying features of the invention can be readily delivered to the desired lumenal location by mounting it on an expandable member of a delivery catheter, for example a balloon, and passing the catheter-stent assembly through a body lumen to an implantation site. A variety of means for securing the stent to the expandable member on the catheter are available.

It will be appreciated that, in the preferred embodiment the expandable rings are coupled together to cooperate in forming an outline of an expandable cylindrical shell. Radial expansion of such shell may be achieved in the undulating pattern expanding its waveform to, in effect, decrease the waveform's amplitude and the frequency. The rings are so constructed as to be expanded to be plastically deformed (except with NiTi alloys) so that the stent itself will remain in its expanded condition and have sufficient rigidity to support the center of the vessel against collapse. During expansion of the stent, the respective one end or the other of the undulating portion of the rings may tip outwardly to extend radially outwardly from the exterior cylindrical outline defined by the expanded stent, when in its unflexed condition to thus slightly radially embed in the wall of the vessel and help secure the expanded stent in its implanted location.

In those embodiments when the stent is constructed of superelastic NiTi alloys, the expansion occurs when the stress of compression is removed so as to allow the phase transformation from martensite back to austenite and as a result the expansion of the stent.

The links which interconnect adjacent cylindrical rings may be constructed with relatively small transverse cross-sections similar to the transverse dimensions of the undulating components of the expandable cylindrical elements and, in other embodiments, may be thinner to further facilitate flexibility. The particular thickness of the links depends on, among other factors, flexibility goals as well as rigidity requirements. The links may be formed in a unitary structure with the expandable cylindrical elements from the same intermediate product, such as a tubular element, or they may be formed independently and connected by suitable means, such as by welding or by mechanically securing the ends of the links to the ends of the expandable cylindrical elements.

The springs which connect the opposite ends of the links joining adjacent cylindrical rings may also have a transverse cross-section similar to the transverse dimensions of the undulating components of the expandable cylindrical elements in some embodiments, while in other embodiments, the cross-section may be thinner. The springs may be formed in a unitary structure with the expandable cylindrical elements from the same intermediate product, such as a tubular element, or they may be formed independently and connected by suitable means, such as by welding or by mechanically securing the ends of the interconnecting elements to the ends of the expandable cylindrical elements. In expansion the springs do not expand similarly to the undulations comprising peaks and valleys. Rather, the springs, comprised of subpeaks and valleys, substantially retain their original shape so as to continue to provide flexibility in the stent after implantation.

The number and location of the springs can be varied in order to develop the desired longitudinal as well as rotational flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site. The number of links can also be varied in order to tailor the stent to specific applications.

The stent may be formed from a tube by laser cutting the pattern of cylindrical rings and links in the tube. The stent may also be formed by laser cutting a flat metal sheet in the pattern of the cylindrical rings and links, and then rolling the pattern into the shape of the tubular stent and providing a longitudinal weld to form the stent.

Other features and advantages of the present invention will become more apparent from the following detailed description of the invention when taken in conjunction with the accompanying exemplary drawings.

DETAILED DESCRIPTION OF THE PREFERRED EMBODIMENTS

The present invention stent improves on existing stents by providing a longitudinally flexible stent having a uniquely designed pattern and novel flexible joints incorporated therein. In addition to providing longitudinal and rotational flexibility, the stent of the present invention also provides radial rigidity and a high degree of scaffolding of a vessel wall, such as a coronary artery. The design of the flexible joints and their placement within the cylindrical rings of the stent provides for uniform scaffolding and a high degree of vessel wall coverage.

Figure 1:
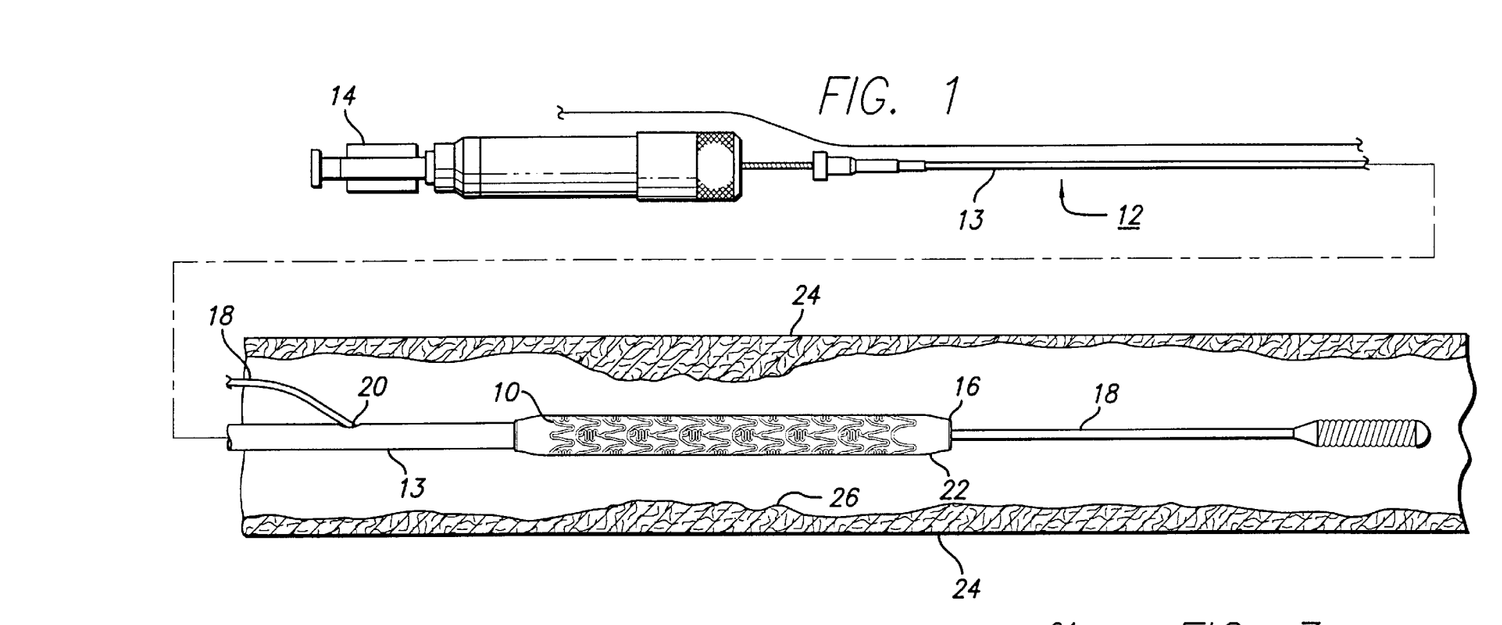
FIG. 1 is an elevational view, partially in section, showing a stent in enlarged scale which embodies features of the invention as mounted on a rapid-exchange delivery catheter and positioned within an artery.

Turning to the drawings, FIG. 1 depicts one embodiment of the present invention stent 10 mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 of the present invention is used to repair a diseased or damaged arterial wall which may include the plaque 26 as shown in FIG. 1, or a dissection, or a flap which are commonly found in the coronary arteries, peripheral arteries and other vessels.

Figure 2:
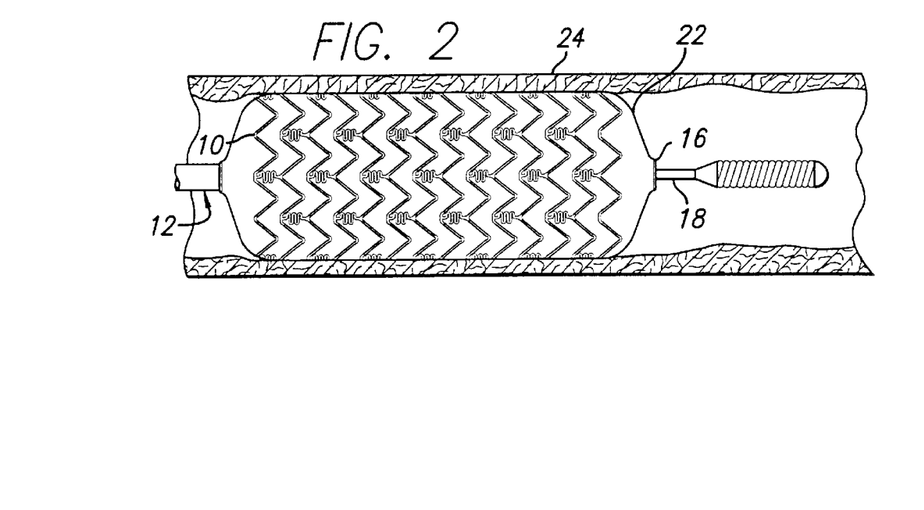
FIG. 2 is a partial sectional view, similar to that shown in FIG. 1 with the stent expanded within the artery to engage the arterial wall.
Figure 3:
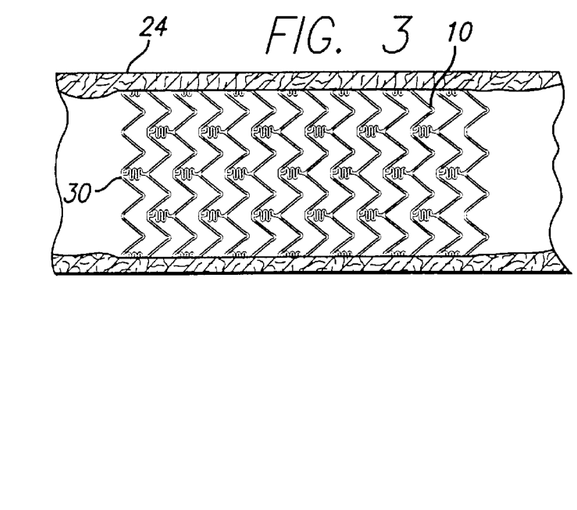
FIG. 3 is a sectional view similar to FIG. 2, showing the expanded stent implanted within the artery after withdrawal of the rapid-exchange delivery catheter.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery after the catheter is withdrawn, as illustrated by FIG. 3. Due to the formation of the stent from an elongated tubular member in this particular embodiment, the undulating components of the stent are relatively thin in transverse cross-section, so that when the stent is expanded, it is pressed into the wall of the artery and as a result does not interfere significantly with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical rings at regular intervals provide uniform support for the wall of the artery, and consequently are well adapted to tack up and hold in place small flaps or dissections in the wall of the artery, as illustrated in FIGS. 2 and 3.

Figure 4:
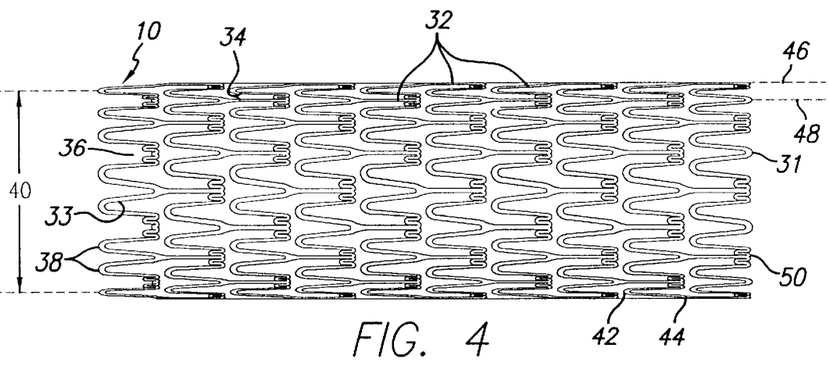
FIG. 4 is a side view of one embodiment of the stent comprising W-shaped undulations and W-shaped springs in an unexpanded state.

In keeping with the present invention, FIGS. 4 through 17 depict stent 10 and alternative embodiments. Turning to FIG. 4, stent 10 is shown in tubular condition so that the pattern can be clearly viewed. The stent is typically formed from a tubular member, however, it can be formed from a flat sheet and rolled into a cylindrical configuration.

As shown in FIG. 4, stent 10 is made up of a plurality of longitudinally spaced expandable cylindrical rings 32 formed by undulations defining respective peaks and valleys, generally designated 31 and 33 arranged generally coaxially and extending circumferentially when the stent 10 is in a tubular form. The cylindrical rings 32 are interconnected by joints, generally designated 50, formed by a combination of links 34 interposed between adjacent cylindrical rings 32 and springs 36. The stent has a relatively small delivery diameter 40 as shown in FIG. 4, and an implanted diameter which is larger. Each cylindrical ring is elongated and terminates at respective opposite proximal and distal ends 42 and 44. Typically, since the stent 10 is laser cut from a solid tube there are no discreet parts in the described cylindrical rings 32.

Referring to FIG. 4, the respective rings are in the form of circumferentially spaced, elongated undulations having respective proximal and distal ends 42 and 44, respectively, all connected together to, in the unflexed state, cooperating to form a network contained within an annular envelope in space relationship and having an outer cylindrical surface depicted by broken lines 46 and an inner cylindrical surface 48.

The flexible joints are formed by links 34 and springs 36 configured with peaks and valleys 41 and 43. The links 34 connect adjacent cylindrical rings 32 together through one or more of the springs 36. The springs 36 couple one end of each link 34 to one ring while the end link 34 is coupled directly to the body of an adjacent ring 32. The flexibility of the springs 36 is dictated by the exterior of the bends defining the respective peaks and valleys 41 and 43 in the springs 36 along with the cross sectional diameter. Thus, as the stent is being delivered through a tortuous vessel, such as a coronary artery, the bends defining the peaks and valleys 41 and 43 of the springs 36 will permit the stent 10 to flex, thus enhancing delivery of the stent to the target site. The number of springs 36 can be increased or decreased from that shown, as demonstrated in other embodiments of the present invention, to achieve differing flexibility characteristics. Additionally, the springs 36 can be located on both ends of the link 34, instead of just one end as mentioned above. With the links 34 being substantially aligned with the longitudinal axis, the springs 36 act like hinges to provide flexibility between the rings 32.

The stent design of the current invention also resists the transfer of rotary force from one ring to the other and thereby reduce the tendency of rotary forces applied to one portion of the stent resulting in bodily rotation of the entire stent. To this end, the springs 36 act like lost motion joints so that when one ring is rotated slightly relative to the next the flexture in the spring connecting the end of the joining links will provide for angular shifting of such links to provide for relatively free rotation of such ring without applying rotary forces to the adjacent ring.

In one embodiment, the stent 10 (FIGS. 4 and 5) can be described more particularly as having a plurality of undulations 38 defined by ring peaks 31 and valleys 33 with either or both such undulations being coupled at their respective peaks and/or valleys with joint springs 36, themselves defined by joint peaks and valleys 41 and 43. Although the stent 10 is not divided into separate elements, for ease of discussion references to undulations 38 comprised of peaks and valleys 31 and 33 and springs 36 comprised of joint peaks 41 and valleys 43 is convenient. The number of undulations 38 and springs 36 can vary in number for each ring 32 depending upon the application. Thus, for example, if the stent 10 is to be implanted in a coronary artery, a lesser number of undulations 38 and springs 36 may be required than if the stent 10 is implanted in a peripheral artery, which has a larger diameter than a coronary artery. In the preferred embodiment, adjacent peaks 41 of the joint springs 36 connect to one end of the respective joining links 34 to provide for relatively free flexing of the respective links to angulate in one direction or the other under application of only minimal forces. As can be seen in FIG. 4, the ring undulation peaks 31 are out of phase, meaning that the adjacent peaks are not aligned along the longitudinal axis of the stent. It may be desirable under certain circumstances to position peaks 31 so that they are in phase, that is, all the rings 32 would be circumferentially aligned with each other. Positioning the undulations 38 and springs 36 in the manner illustrated in FIG. 4 provides a stent with uniform expansion capabilities, high radial strength, a high degree of flexibility, and sufficient wall coverage to support the vessel.

Each radially expandable cylindrical element of the stent 10 may be substantially independently expanded. Therefore, the balloon 22 may be provided with an inflated shape other than cylindrical, e.g., tapered, to facilitate implantation of the stent 10 in a variety of lumenal shapes. This can also be applied to the other embodiments illustrated in FIGS. 6 through 17.

The stent 10 has a plurality of cylindrical rings 32, each formed by a series of circumferential large W-shaped undulations 3 8 incorporating longitudinal legs 39 connected at their respective opposite extremities by ring peaks and/or valleys 31 and 33, one or the other being formed with the respective undulating but smaller spring 36. Again, while the stent 10 is generally laser cut from a solid tube and typically has no discreet parts, for ease of identification the stent 10 can be referred to as having large W-shaped undulations 38 and smaller W-shaped springs 36. The combination of springs 36 and links 34 comprise the flexible joints 50. The springs 36 have a smaller cross-section than the cross-section of the links 34 or the W-shaped undulations 38 of the rings 32 in this particular embodiment. The small cross-section of the springs 36 enables them to flex more freely and allow the stent 10 to bend accordingly. The features are more prominently displayed in FIG. 5. The W-shaped undulations 38 are connected through the link 34 to the smaller W-shaped springs 36. Preferably one end of the link 34 is contained within W-shaped spring 36, which should be wide enough to accommodate the link 34 when the stent 10 is crimped so that no portion of the link 34 and the W-shaped spring 36 overlap. Preferably, the W-shaped undulation 38, the link 34 and the W-shaped spring 36 are in the same cylindrical plane as defined by the cylindrical outer wall surface 46 and the cylindrical inner wall surface 48.

Figure 5:
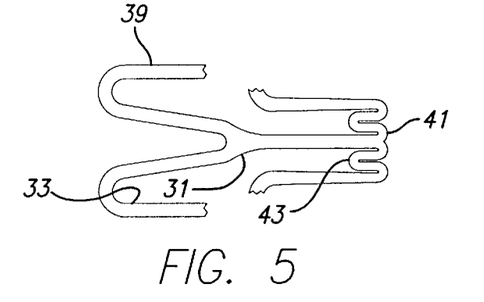
FIG. 5 is an enlarged fragmentary view of a portion of the stent shown in FIG. 4 depicting a link connecting the W-shaped undulations and W-shaped springs in adjacent cylindrical rings.

The configuration of the present embodiment represents a combination of flexibility and supported surface area capability. More particularly, the arrangement of a large W-shaped undulation 38 connected directly to link 34 which in turn is connected to an adjacent ring 32 through a W-shaped spring 36 located on the adjacent ring 32 provides flexibility and support. The spring 36 gives the flexibility while the substantially rigid large W-shaped undulation 38 provides support.

The ring undulations 38 are so configured and joined with the links 34 that, when the delivery balloon 22 applies radially outward forces to the rings, the undulations 38 will be caused to tilt to project at a small angle relative to the longitudinal axis so that the free ends defined by the respective peaks angle radially outwardly beyond the annular surface 46 (FIG. 4).

Figure 6:
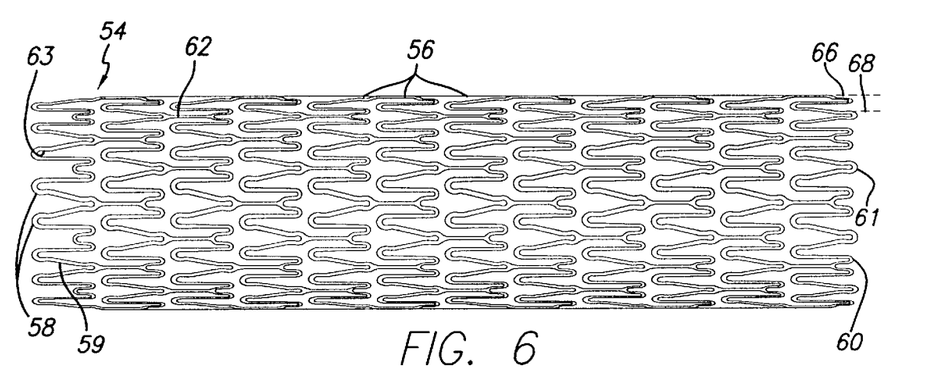
FIG. 6 is a side view of one embodiment of the stent comprising W-shaped undulations and W-shaped springs in an unexpanded state.

Another embodiment of the present invention shown in FIG. 6 illustrates a stent 54 comprised of cylindrical rings 56 formed of large W-shaped ring undulations 58 incorporating longitudinal legs 59 connected at their respective opposite extremities by ring peaks and/or valleys 61 and 63, one or the other being coupled with the respective undulating but smaller W-shaped spring 60. The valleys 63 and small W-shaped springs 60 incorporate smaller joint peaks 65 and valleys 67 (shown in FIG. 7). The springs 60 together with the links 62 comprise the flexible joints 64. Here, the large W-shaped undulations 58 and springs 60 are connected to each other through the link 62. The peak 61 of the W-shaped undulation 58 is connected through the link 62 to the smaller peak 65 of the W-shaped spring 60. Preferably, link 62 is contained within the W-shaped spring 60, which should be wide enough to accommodate link 62 when the stent 54 is crimped so that no portion of the link 62 and the W-shaped spring 60 overlap. Preferably, the large W-shaped undulation 58, the link 62 and the small W-shaped spring 60 are in the cylindrical shell defined by the cylindrical outer wall surface 66 and the cylindrical inner wall surface 68.

Figure 7:
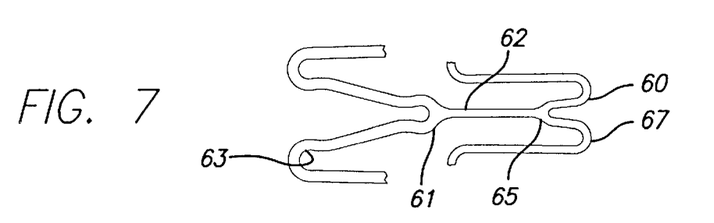
FIG. 7 is an enlarged fragmentary view of the stent shown in FIG. 6 depicting a link connecting the W-shaped undulations and W-shaped springs in adjacent cylindrical rings.

Both the W-shaped springs 60 and the links 62 of the present embodiment have smaller cross-sections than those of the larger W-shaped undulations 58 of the rings 56. As mentioned above, the small cross-section of the spring 60 enables it to be flexible. The small cross-section of the link 62 enables it to be more flexible along with lessening the possibility of interference with other sections of the stent 54.

The ring undulations 58 are so configured and joined with the links 62 that, when the delivery balloon 22 applies radially outward forces to the rings, the undulations 58 will be caused to tilt to project at a small angle relative to the longitudinal axis so that the free ends defined by the respective peaks 61 angle radially outwardly beyond the annular surface 66 (FIG. 6).

Figure 8:
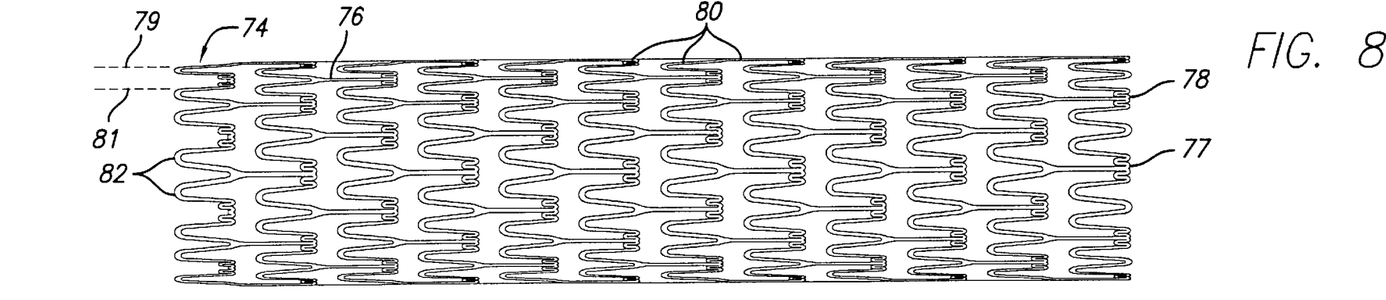
FIG. 8 is a side view of one embodiment of the stent comprising W-shaped undulations, W-shaped springs and lengthened links in an unexpanded state.
Figures 9, 10, 11:
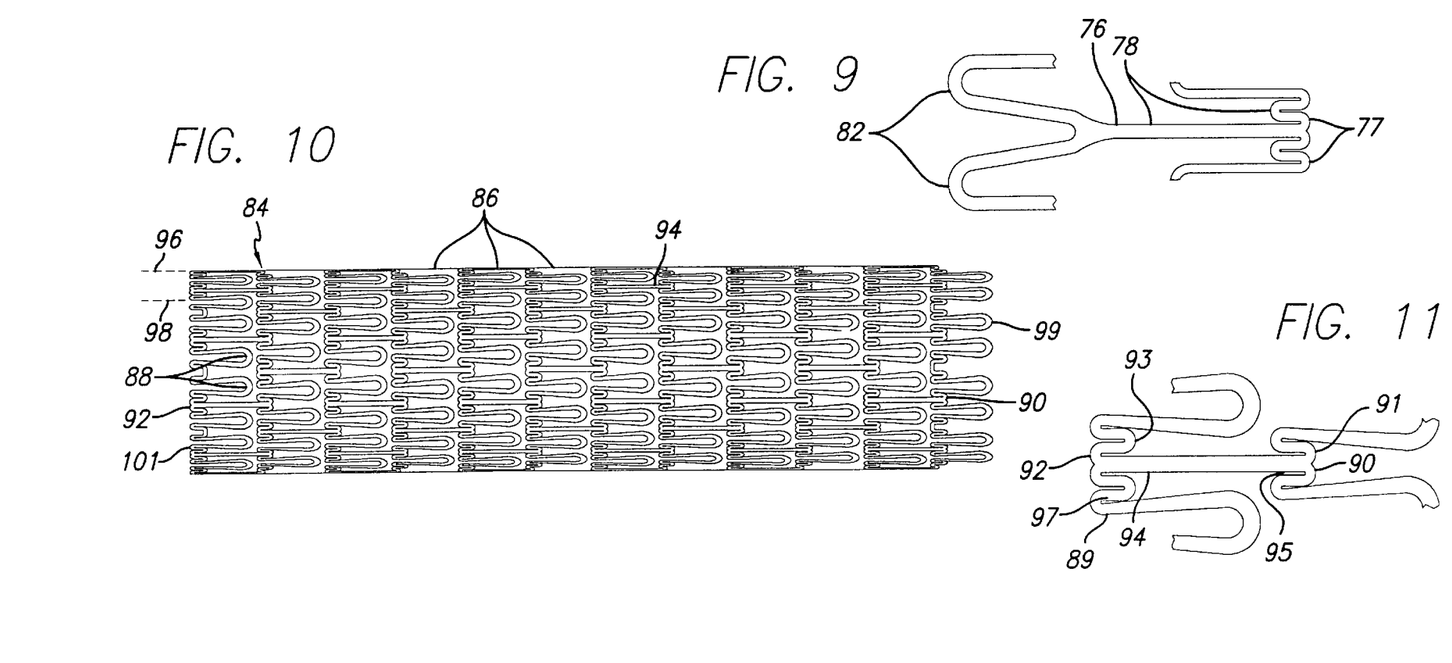
FIG. 9 is an enlarged fragmentary view of a portion of the stent shown in FIG. 8 depicting the lengthened link connecting the W-shaped undulations and W-shaped springs in adjacent cylindrical rings.
FIG. 10 is a side view of one embodiment of the stent comprising U-shaped undulations and U and W-shaped springs in an unexpanded state.
FIG. 11 is an enlarged detail view of a portion of the stent shown in FIG. 10 depicting a link connecting the U-shaped undulations and U and W-shaped springs in adjacent cylindrical rings.

The stent 74 shown in FIGS. 8 and 9 is similar to the stents illustrated in FIGS. 4 and 5 as described above. The main difference with this embodiment is that the links 76 included in the flexible joints 78 are longer. This extended link length prevents adjacent rings 80 from overlapping when the stent 74 is substantially bent. This bending situation can occur during insertion or implantation of the stent 74 in a tightly curved portion of the anatomy. Although the surface area of the vessel which the stent 74 can support is smaller than if the rings 80 were more closely spaced together, the W-shaped undulations 82 are large enough that even when the rings 80 are spaced apart, they provide sufficient support. Furthermore, because the links 76 effectively space the rings apart, less rings will be needed to cover a preset determined length of a vessel. The smaller number of rings 80 will result in cost savings due to reduced material and reduced manufacturing time. Preferably, the large W-shaped undulation 82, the link 76 and the small W-shaped spring 77 are in the cylindrical shell defined by the cylindrical outer wall surface 79 and the cylindrical inner wall surface 81.

In another embodiment of the present invention illustrated in FIGS. 10 and 11, the stent 84 can be described as having cylindrical rings 86 formed of large U-shaped undulations 88 defined by ring peaks 99 and valleys 101 and incorporating longitudinal legs 89 and small U and W-shaped springs 90 and 92 defined by joint peaks 91 and 93 and valleys 95 and 97,respectively. The springs 90, along with links 94 comprise the flexible joints 96. The small U and W-shaped springs 90 and 92 are connected to each other through the link 94. In this embodiment the springs 90 and 92 are constructed with cross-sections thinner than those of the U-shaped undulations 88 or the links 94. The small cross-section of the springs 90 enables them to flex more freely and allows the stent 84 to bend accordingly. The small U and W-shaped springs 90 and 92 are coupled to adjacent rings 86. Preferably, link 94 is contained within W-shaped spring 94 on one end and a U-shaped undulation 88 on the other, both of which should be wide enough to accommodate the link 94 when the stent 84 is crimped so that no portion of the links and the U or W-shaped springs 90 and 92 overlap. The W-shaped undulations 88 are connected to the springs 90 and 92 of adjacent rings 86. Preferably, the W-shaped undulation 88, the link 94 and the W-shaped springs 90 and 92 are in the same cylindrical shell as defined by the cylindrical outer wall surface 96 and the cylindrical inner wall surface 98.

Two large U-shaped undulations 88 of one ring 86 are coupled together by either a U-shaped spring 90 or a W-shaped spring 92. The pattern is such that the U and W-shaped springs 90 and 92 alternate in connecting the U-shaped undulations 88 of each ring 86. Flexibility is provided through the springs 90 and 92 while the vessel wall surface is sufficiently supported with the relatively more rigid large U-shaped undulations 88. This particular embodiment provides for enhanced flexibility due to the combination of U and W-shaped springs 90 and 92 connecting each end of the link 94. In other words, neither end of the link 94 is rigidly coupled with the stent 84 and the resultant flexibility is high.

The ring undulations 88 are so configured and joined with the links 94 that, when the delivery balloon 22 applies radially outward forces to the rings, the undulations 88 will be caused to tilt to project at a small angle relative to the longitudinal axis so that the free ends defined by the respective peaks 99 angle radially outwardly beyond the annular surface 46 (FIG. 10).

Figures 12, 13, 14, 15:
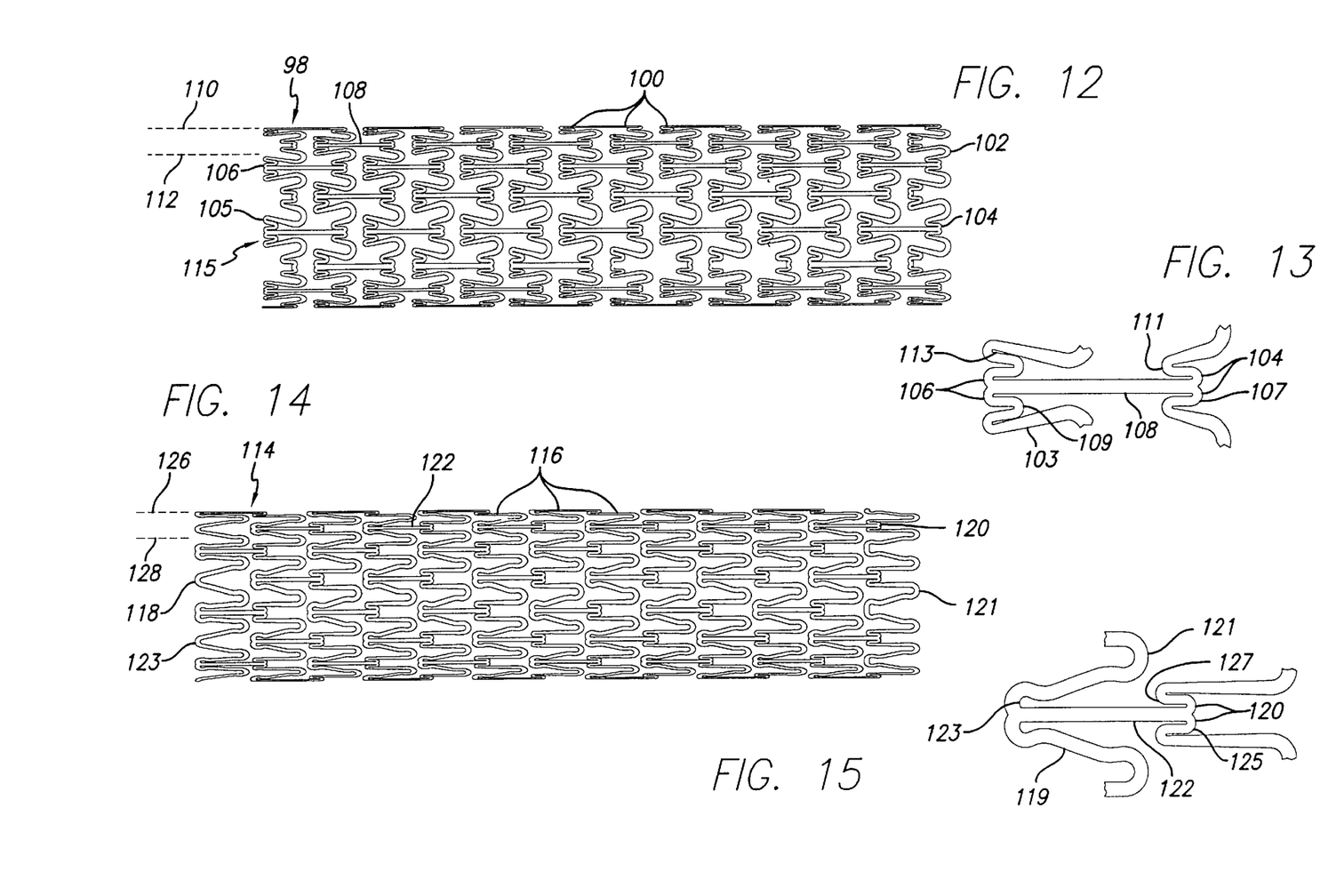
FIG. 12 is a side view of one embodiment of the stent depicting W-shaped undulations and U-shaped springs in an unexpanded state.
FIG. 13 is an enlarged detail view of a portion of the stent shown in FIG. 11 depicting a link connecting W-shaped undulations and U-shaped springs in adjacent cylindrical rings.
FIG. 14 is a side view of one embodiment of the stent depicting W-shaped undulations and U-shaped springs in an unexpanded state.
FIG. 15 is an enlarged detail view of a portion of the stent shown in FIG. 14 depicting a link connecting the W-shaped undulations and U-shaped springs in adjacent cylindrical rings.

In another embodiment of the present invention illustrated in FIGS. 12 and 13, the stent 98 can be described as having cylindrical rings 100 formed of large U-shaped undulations defined by ring peaks 102 and valleys 105 and incorporating longitudinal legs 103 and small U and W-shaped springs 104 and 106 defined by smaller joint peaks 107 and 109 and valleys 111 and 113, respectively. The springs 104 and 106 have smaller cross-sections than links 108 or the U-shaped undulations 102. The small cross-section of the springs 104 and 106 enables them to flex more freely and allow the stent 98 to bend accordingly. The springs 104 and 106 and links 108 comprise the flexible joints 115. The large U-shaped undulations 102 are circumferentially connected to each other through both small U and W-shaped springs 104 and 106. In this embodiment, the W-shaped springs 104 and 106 are connected through the link 108 to the U-shaped springs 104 and 106. Notably, in this embodiment, the links 108 connect only the springs 104 and 106 of adjacent rings 100 as opposed to connecting to both springs and undulations as in other embodiments. Preferably, one end of the link 108 is contained within the U-shaped undulation 102 and the other end is contained within the W-shaped spring 106, each of which should be wide enough to accommodate each end of the link 108 when the stent is crimped so that no portion of the link 108 and the U or W-shaped springs 104 and 106 overlap. The U-shaped undulations 102 are connected to the W-shaped springs 104 and 106 of adjacent rings 104 which also form a W-shaped 102. Preferably, the U-shaped undulation 102, the link 108 and the U and W-shaped springs 104 and 106 are positioned in the same cylindrical shell as defined by the cylindrical outer wall surface 110 and the cylindrical inner wall surface 112.

The configuration of the present embodiment represents a combination of flexibility and supported surface area capability. More particularly, the arrangement of a large U-shaped undulation 102 of one ring 100 abutted by a U-shaped spring 104 on one end and a W-shaped spring 106 on the other end provides flexibility while maintaining high supported surface area with the substantially rigid and large U-shaped undulations 102.

The ring undulations 102 are so configured and joined with the links 108 that, when the delivery balloon 22 applies radially outward forces to the rings, the undulations 102 will be caused to tilt to project at a small angle relative to the longitudinal axis so that the free ends defined by the respective peaks 102 angle radially outwardly beyond the annular surface 110 (FIG. 12).

In another embodiment illustrated in FIGS. 14 and 15, the stent 114 can be described as having cylindrical rings 116 formed of large W-shaped undulations 118 defined by ring peaks 121 and valleys 123 and incorporating longitudinal legs 119 and small U-shaped springs 120 defined by smaller joint peaks 125 and valleys 127. The springs 120 and links 122 comprise flexible joints. The springs 120 have a smaller cross-section than the links 122 or the W-shaped undulations 118. The small cross-section of the springs 120 enables them to flex more freely and allow the stent 114 to bend accordingly. The large W-shaped undulations 118 and small U-shaped springs 120 are connected to each other through the link 122. Preferably, the link 122 is contained within the U-shaped spring 120 which should be wide enough to accommodate the link 122 when the stent 114 is crimped so that no portion of the link 122 and the U-shaped spring 120 overlap. The other end of the link 122 is connected to the W-shaped undulation 118. Preferably, the W-shaped undulation 118, the link 122 and the U-shaped spring 120 are in the same cylindrical plane as defined by the cylindrical outer wall surface 126 and the cylindrical inner wall surface 128.

The ring undulations 118 are so configured and joined with the links 122 that, when the delivery balloon 22 applies radially outward forces to the rings, the undulations 118 will be caused to tilt to project at a small angle relative to the longitudinal axis so that the free ends defined by the respective peaks 125 angle radially outwardly beyond the annular surface 126 (FIG. 14).

Figure 16:
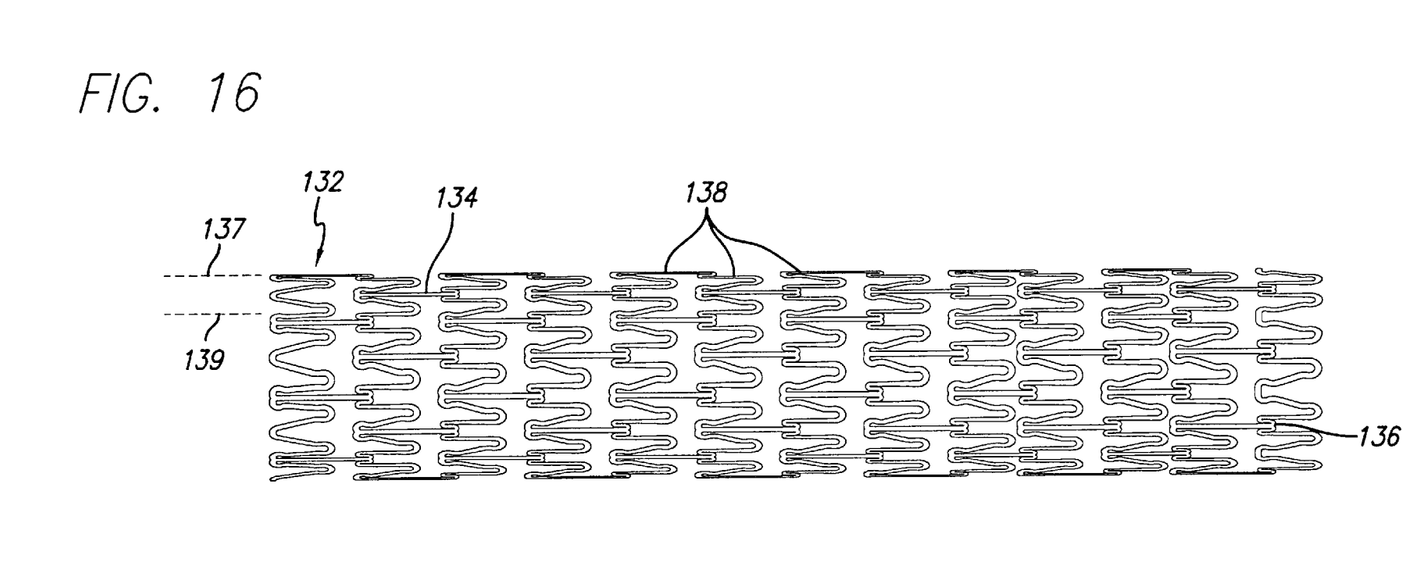
FIG. 16 is a side view of one embodiment of the stent depicting W-shaped undulations, U-shaped springs and a lengthened link in an unexpanded state.
Figure 17:
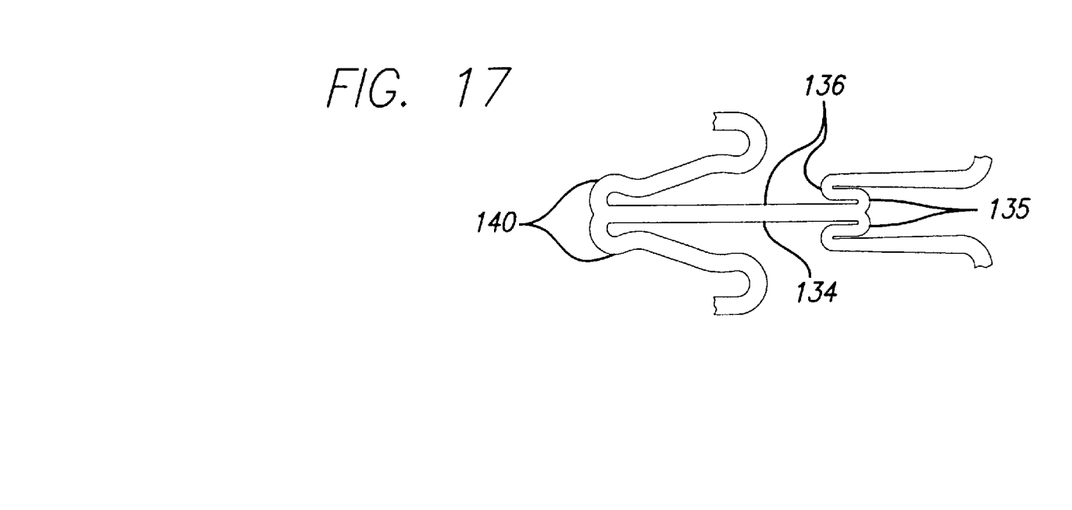
FIG. 17 is an enlarged detail view of a portion of the stent shown in FIG. 16 depicting an the lengthened link connecting the W-shaped undulations and U-shaped springs in adjacent cylindrical rings.

The stent 132 illustrated in FIGS. 16 and 17 is similar to the stent described above and illustrated in FIGS. 14 and 15. The main difference between this embodiment of the present invention and that mentioned previously and illustrated in FIGS. 14 and 15 is that the links 134 which are included in the flexible joints 136 here are longer. This extended link length prevents adjacent rings 138 from overlapping with each other when the stent 132 is bent. This bending situation can occur during insertion or implantation of the stent 132 in a tightly curved portion of the anatomy. Although the surface area of the vessel which the stent can support is smaller than if the rings 138 were more closely spaced together, W-shaped undulations 140 are large enough that even when the rings are spaced apart, they provide sufficient support in appropriate applications. Further, because the links 134 effectively space the rings 138 apart, less rings will be needed to cover a preset determined length of a vessel. The small number of rings will translate to cost savings because of reduced material and reduced manufacturing time needed. Preferably, the large W-shaped undulation 140, the link 134 and the small U-shaped spring 135 are in the cylindrical shell defined by the cylindrical outer wall surface 137 and the cylindrical inner wall surface 139.

In one important aspect of the invention, after the stent is implanted in a coronary artery, or other vessel, because of its novel design, the cylindrical rings have the ability to flex radially as the vessel pulsates when blood pumps through it. Likewise, because of the novel and unique design of flexible joints, as the vessel moves and pulsates from the pumping blood, the stent can flex longitudinally. The radial and longitudinal flexing of the stent reduces the likelihood that the stent will cause injury to the intima of a coronary artery, which also may have a tendency to reduce the likelihood of restenosis.

The stent of the present invention can be made in many ways. One method of making the stent is to cut a thin-walled tubular member, formed from stainless steel, cobalt-chromium, tantalum, titanium, or nickel-titanium tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

The tubing may be made of suitable biocompatible material such as stainless steel. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

The tubing is mounted in a rotatable collet fixture of a machine-controlled apparatus for positioning the tubing relative to a laser. According to machine-encoded instructions, the tubing is rotated and moved longitudinally relative to the laser which is also machine controlled. The laser selectively removes the material from the tubing by ablation and a pattern is cut into the tube. The tube is therefore cut into the discrete pattern of the finished stent.

The process of cutting a pattern for the stent into the tubing is automated except for loading and unloading the length of tubing. In one example, a CNC-opposing collet fixture for axial rotation of the length of tubing is used in conjunction with a CNC X/Y table to move the length of tubing axially relatively to a machine-controlled laser. The entire space between collets can be patterned using the $CO_2$ laser set-up of the foregoing example. The program for control of the apparatus is dependent on the particular configuration used and the pattern to be ablated in the coating.

Cutting a fine structure (0.0035" web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes are made typically of stainless steel with an outside diameter of 0.060" to 0.066" and a wall thickness of 0.002" to 0.004". These tubes are fixtured under a laser and positioned utilizing a CNC to generate a very intricate and precise pattern. Due to the thin wall and the small geometry of the stent pattern (0.0035" typical web width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd-YAG, typically available from Quantronix of Hauppauge, N.Y., that is frequency doubled to produce a green beam at 532 nanometers is utilized. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system of the present invention makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018" I.D.) is centered around the focused beam with approximately 0.010" between the tip of the nozzle and the tubing. The jet is pressurized with oxygen at 20 psi and is directed at the tube with the focused laser beam exiting the tip of the nozzle (0.018" dia.). The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034" dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005") with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCL for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCL for 1–4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structure are rinsed in water. They are now ready for electropolishing.

The stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110°–1350° F. and the current density is about 0.4 to about 1.5 amps per in.$^2$. Cathode to anode area should be at least about two to one. The stents may be further treated if desired, for example by applying a biocompatible coating.

It will be apparent that both focused laser spot size and depth of focus can be controlled by selecting beam diameter and focal length for the focusing lens. It will be apparent that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process essentially provides stent cross-sections, from cut-to-cut, which are square or rectangular, rather than trapezoidal. The cross-sections have generally perpendicular edges formed by the laser cut. The resulting stent structure provides superior performance.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as superelastic and shape memory alloys. Superelastic and shape memory alloys are well known and include, but are not limited to, nickel titanium and nickel/titanium/vanadium. Any of the superelastic or shape memory alloys can be formed into a tube and laser cut in order to form the pattern of the stent of the present invention. As is well known, the shape memory and superelastic alloys of the stent of the present invention can include the type known as thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of undulations per ring, materials used, and the like have been described herein and are provided as examples only. Other modifications and improvements may be made without departing from the scope of the invention.

What is claimed:

1. A flexible intravascular stent for use in a body lumen, comprising:

a plurality of rings spaced longitudinally along a common longitudinal axis;

each ring having a plurality of longitudinal undulations configured with respective ring peaks and valleys;

springs formed in the ring peaks by undulating spring sections;

links having a first end connected to the respective springs; and the links and springs joining adjacent rings together.

2. The stent of claim 1, wherein at least some of the ring undulations are formed as W-shaped members.

3. The stent of claim 1, wherein at least some of the springs are formed as W-shaped members.

4. The stent of claim 2, wherein the plurality of links connect W-shaped springs to undulations within adjacent cylindrical rings.

5. The stent of claim 1, wherein the plurality of undulations and springs are arranged circumferentially in a repeating pattern wherein W-shaped undulations are followed by W-shaped springs followed by W-shaped undulations.

6. The stent of claim 5, wherein at least some of the links have a smaller cross-section than that of some of the W-shaped undulations.

7. The stent of claim 5, wherein the W-shaped springs have a smaller cross-section than that of the W-shaped undulations.

8. The stent of claim 5, wherein the W-shaped undulations each have a predetermined longitudinal length and the links have a longitudinal length longer than the predetermined length.

9. The stent of claim 1, wherein the stent is formed from a biocompatible material selected from the group consisting of stainless steel, tantalum, titanium, cobalt-chromium, NiTi alloys, and thermoplastic polymers.

10. The stent of claim 1, wherein the stent is formed from a single piece of tubing.

11. The stent of claim 1, wherein the stent is coated with a biocompatible coating.

12. The stent of claim 1, wherein at least some of the springs are formed as undulations.

* * * * *